United States Patent [19]
Domergue

[11] 3,994,907
[45] Nov. 30, 1976

[54] COUMARIN DERIVATIVES, THEIR PREPARATION AND THEIR USE AS OPTICAL BRIGHTENING AGENTS

[75] Inventor: Annick Marthe Suzanne Simone Domergue, Eaubonne, France

[73] Assignee: Produits Chimiques Ugine Kuhlmann, Paris, France

[22] Filed: Jan. 14, 1975

[21] Appl. No.: 540,774

[30] Foreign Application Priority Data
Jan. 29, 1974  France............................ 74.02809

[52] U.S. Cl. ................ 260/295 F; 260/240 D;
260/294.8 C; 260/307 G; 260/564 G;
252/301.28
[51] Int. Cl.². ....................... C07D 413/14
[58] Field of Search ............. 260/295 F, 307 G

[56] References Cited
OTHER PUBLICATIONS
Davison et al., Chem. Abstracts, vol. 78(8) Item No. (45,068e) Feb. 26, 1973.

*Primary Examiner*—Alan L. Rotman
*Attorney, Agent, or Firm*—Beveridge, DeGrandi, Kline & Lunsford

[57] ABSTRACT
Coumarin of the formula:

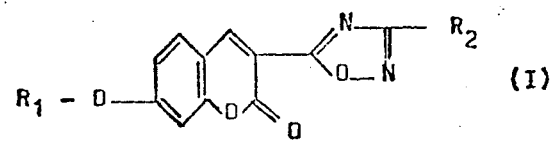

in which $R_1$ represents an alkyl group having 1 to 5 carbon atoms, and either unsubstituted or substituted by a non-ionic and non-chromophoric group, $R_2$ represents a benzene, styryl or heterocyclic residue such residue being unsubstituted or substituted by one or two non-ionic and non-chromophoric groups; process for the preparation of a coumarin of the above formula which comprises reacting an orthohydroxybenzaldehyde of formula (II) upon an acid of formula (III) or one of its functional derivatives:

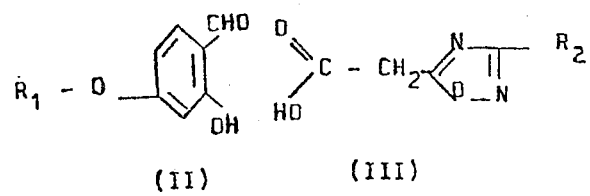

wherein $R_1$ and $R_2$ have the same definitions as in claim 1; process for the fluorescent brightening of fibrous material of synthetic origin which comprises treating the material with a coumarin of the above formula; fluorescent brightening composition containing a coumarin of the above formula and a dispersing agent resulting from the condensation of naphthalenesulphonic acids with formaldehyde in the presence of or absence of phenol compounds, said dispersing agent comprising 30% to 50% monosulphonated condensates, 30% to 50% disulphonated condensates and 10% to 40% trisulphonated or higher polysulphonated condensates; fibres of synthetic origin treated with a coumarin of the above formula or with a brightening composition as set out above.

9 Claims, No Drawings

COUMARIN DERIVATIVES, THEIR PREPARATION AND THEIR USE AS OPTICAL BRIGHTENING AGENTS

This invention relates to new coumarin derivatives, to their preparation and to their use as optical brightening agents.

It has already been proposed to use as fluorescent brightening agents 7-alkoxy coumarins which are variously substituted in the 3 position for example by a 4-benzotriazolyl(2) phenyl radical (U.S. Pat. No. 3,288,804), by a triazolyl radical (U.S. Pat. No. 3,271,412), by a 2-benzimidazolyl radical (U.S. Pat. No. 3,014,041), or by a para-cyanophenyl radical (U.S. Pat. No. 3,525,753). However, on polyester fibres these compounds generally produce bluing effects which veer towards green or are not efficient enough.

However, in accordance with the present invention, it is possible to obtain a remarkable brightening effect with excellent general fastness on fibres of synthetic origin, in particular on fibres based on polyesters, polyamides or cellulose esters.

According to the present invention therefore coumarins are provided of the general formula:

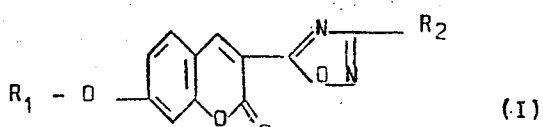

(I)

in which $R_1$ represents an alkyl group having 1 to 5 carbon atoms, possibly substituted by a non-ionic and non-chromophoric group, $R_2$ represents a benzene, styryl or heterocyclic residue possibly carrying one or two non-ionic and non-chromophoric substituents.

The non-ionic and non-chromophoric group which may possibly be carried by the alkyl group $R_1$ may be, for example, a halogen atom, preferably chlorine or bromine, or a hydroxy or alkoxy group containing 1 to 4 carbon atoms (preferably methoxy or ethoxy).

Possible non-ionic and non-chromophoric substituents for the residue $R_2$ are halogen atoms (preferably chlorine or bromine), alkyl or alkylsulphonyl groups containing 1 to 4 carbon atoms, and alkoxy or fluoroalkoxy groups containing 1 to 4 carbon atoms, such as methoxy, ethoxy, difluoromethoxy trifluoromethoxy or trifluoroethoxy groups.

When $R_2$ represents a heterocyclic residue, this residue is preferably the residue of a 5- or 6-membered heterocycle containing 1 to 3 heteroatoms. Examples of $R_2$ heterocyclic residues are, more particularly, pyridyl, pyrazolyl and oxadiazolyl residues. This heterocyclic residue may possibly be joined to the oxadiazolyl nucleus of formula (I) by way of a phenylene link such as, for example, in the case of the 3',5'-dimethyl-4-pyrazolyl (1')-phenyl residue.

The compounds of formula (I), in which $R_2$ represents an unsubstituted phenyl group or an ortho-substituted phenyl group, have proved to be particularly interesting.

The compounds of formula (I) may be obtained for example by various known processes for synthesizing coumarins, for example, by the reaction of an ortho-hydroxy-benzaldehyde of formula (II) upon an acid of formula (III) or one of its functional derivatives,

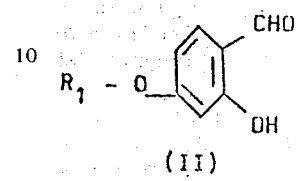

(II)

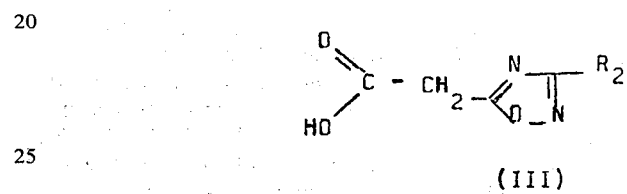

(III)

wherein $R_1$ and $R_2$ have the meanings as given above. The functional derivatives of the acid formula (III) may be, for example, an alkali metal salt, nitrile or a methyl or ethyl ester.

The compounds according to the invention of formula (I) may also be prepared by condensing a coumarin of formula (IV) on an amidoxime of formula (V),

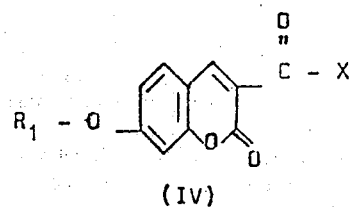

(IV)

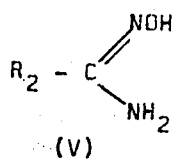

(V)

wherein $R_1$ and $R_2$ have the same meanings as given above and X represents a halogen atom.

The compounds of formula (III) may be prepared for example according to known processes, for example, by reacting an amidoxime of formula (V), in which $R_2$ has the meaning as indicated above, with a functional derivative of malonic acid, for example a monocarboxyhalide of ethyl malonate.

The amidoximes of formula (V) may themselves be obtained for example by reacting hydroxylamine with an $R_2$ – CN nitrile wherein $R_2$ has the same meaning as given above.

The coumarins of formula (IV) may be prepared for example according to known processes, for example by condensing an ortho-hydroxybenzaldehyde of formula (II) with malonic acid or one of its functional derivatives, then by converting the carboxylic group, which is fixed in the 3 position, into carboxyhalide, in particular into carboxychloride by means of thionyl chloride.

The compounds of formula (I) according to the invention are pale yellow or almost white powders which are insoluble in water and soluble in organic media such as for example, alcohols, dioxane and aromatic hydrocarbons where they exhibit very bright violet-blue fluorescence.

To brighten fibrous synthetic material, in particular polyester fibres, the compounds according to the invention are used in the form of aqueous dispersions. The dispersing agents preferably used for putting the compounds of formula (I) in dispersed form are the products resulting from the condensation of naphthalene-sulphonic acids with formaldehyde in the presence or absence of phenol compounds and comprising 30% to 50% monosulphonated condensates, 30% to 50% disulphonated condensates and 10% to 40% trisulphonated or higher polysulphonated condensates. It has in fact been found that these products, whose preparation is described in French Pat. No. 2,122,710, do not alter the white effect produced by the compounds of formula (I) and, in this respect, are superior to conventional dispersing agents, in particular the condensates of the naphthalenesulphonic acid formaldehyde type containing more than 55% trisulphonated or higher polysulphonated products which do not enable the optimum white effect to be obtained.

The concentration of brightening agent may vary, for example from 0.005% to 0.5% relative to the weight of the fibrous material. The brightening action may be effected for example by dyeing under pressure, for example between 120° C. and 130° C. or at boiling point at ordinary pressure in the presence of a swelling agent for the fibre.

The fibres which have been treated with the compounds according to the invention exhibit a magnificent brightening effect and also excellent general fastness, in particular to light.

The invention is illustrated by the following Examples in which parts and percentages are parts and percentages by weight unless otherwise stated.

EXAMPLE 1

7.6 parts of 2-hydroxy-4-methoxy benzaldehyde and 11.6 parts of the ethyl ester of 3-phenyl-1,2,4-oxadiazole-5-acetic acid (boiling point: 150° C/0.5 mm) are dissolved in 80 parts of toluene. 0.5 part of piperidine is added and the mixture is heated under reflux for 1 hour. The mixture is cooled, the crystallized product is filtered and then washed in ethanol. 13.7 parts of 7-methoxy 3-(3-phenyl 1,2,4-oxadiazol-5-yl) coumarin are obtained which, after crystallization in an ethanol-dioxane mixture, melts at 215° C.

| Analysis: | C % | H % | N % |
| --- | --- | --- | --- |
| Calculated for $C_{18}H_{12}N_2O_4$: | 67.5 | 3.75 | 8.76 |
| Found : | 67.7 | 3.82 | 8.77 |

EXAMPLE 2

5 parts of 2-hydroxy-4-ethoxy benzaldehyde and 7 parts of the ethyl ester of 3-phenyl-1,2,4-oxadiazole-5-acetic acid are dissolved in 80 parts of ethanol, then 0.3 part of piperidine is added. The mixture is heated under reflux for one hour, then the precipitate obtained after cooling is filtered. 8 parts of 7-ethoxy-3-(3-phenyl 1,2,4-oxadiazol-5-yl) coumarin are obtained which melts at 229° C. after crystallization in dioxane.

| Analysis: | C % | H % | N % |
| --- | --- | --- | --- |
| Calculated for $C_{19}H_{14}N_2O_4$: | 68.26 | 4.19 | 8.38 |
| Found: | 68.7 | 4.26 | 8.41 |

EXAMPLE 3

4.5 parts of 2-hydroxy-4-methoxy benzaldehyde and 7.38 parts of the ethyl ester of 3-p-tolyl-1,2,4-oxadiazol-5-acetic acid (melting point: 56° C) are dissolved in 80 parts of ethanol. 0.3 part of piperidine is added and the mixture is heated for 1 hour under reflux. After cooling, the crystalline precipitate obtained is filtered and washed in ethanol. Thus 8.5 parts of 7-methoxy-3-(3-p-tolyl-1,2,4-oxadiazol-5-yl) coumarin are obtained which melts at 227° C.

| Analysis: | C % | H % | N % |
| --- | --- | --- | --- |
| Calculated for $C_{19}H_{14}N_2O_4$: | 68.26 | 4.19 | 8.38 |
| Found: | 68.2 | 4.19 | 8.26 |

EXAMPLE 4

4.8 parts of 3-chloroformyl-7-methoxy coumarin (melting point: 143° C) and 2.72 parts of benzamidoxime (Melting point: 77° C) are put in suspension in 100 parts of toluene. The mixture is stirred for 1 hour at ambient temperature, then heated under reflux for 2 hours. After cooling the product obtained is filtered, dried and then refluxed for one hour with 50 parts of acetic acid. The crystals obtained after cooling are filtered. Thus, 4 parts of a compound, which is identical to that of Example 1 with a melting point of 215° C. are obtained.

EXAMPLE 5

The same operation is carried out as in Example 4, but the benzamidoxime is replaced by 3.3 parts of para-methoxy-benzamidoxime (melting point: 122° C). 4.1 parts of 7-methoxy-3-[3-(4-methoxphenyl)-1,2,4-oxadiazol-5-yl] coumarin are obtained which melts at 230° C.

| Analysis: | C % | H % | N % |
| --- | --- | --- | --- |
| Calculated for $C_{19}H_{14}N_2O_5$: | 65.14 | 4.00 | 8.00 |
| Found: | 65.25 | 3.99 | 7.82 |

EXAMPLE 6

By replacing the benzamidoxime in Example 4 by 3.4 parts of ortho-chloro-benzamidoxime (melting point: 112° C) one obtains 4 parts of 7-methoxy-3-[3-(2-chloro phenyl)-1,2,4-oxadiazol-5-yl] coumarin which melts at 183° C.

| Analysis: | C % | H % | N % | Cl % |
|---|---|---|---|---|
| Calculated for $C_{18}H_{11}N_2O_4Cl$: | 60.93 | 3.10 | 7.89 | 10.01 |
| Found: | 60.77 | 3.01 | 7.58 | 10.10 |

The following Table gives other Examples of coumarins according to the invention ($R_1$ = methyl), which have been prepared by using the same operation as that carried out in Example 4 but replacing the benzamidoxime by an equimolar quantity of the corresponding amidoxime of formula (V).

| | | | | Elementary Analysis | | | |
|---|---|---|---|---|---|---|---|
| Ex | $R_2$ | Melting point | | C % | H % | N % | F or Cl % |
| 9 | 4-bromo phenyl | 286° C | Calculated | 54.1 | 2.75 | 7.0 | |
| | | | Found | 54.3 | 2.9 | 7.1 | |
| 10 | 3-pyridinyl | 260° C | Calculated | 63.5 | 3.42 | 13.0 | |
| | | | Found | 63.4 | 3.4 | 12.7 | |
| 11 | 4-trifluoromethoxy phenyl | 205° C | Calculated | 56.4 | 2.72 | 6.93 | 14.1 |
| | | | Found | 56.7 | 2.7 | 6.9 | 14.0 |
| 12 | 4-chloro phenyl | 300° C | Calculated | 60.9 | 3.10 | 7.9 | 10.0 |
| | | | Found | 61.3 | 3.2 | 7.8 | 10.4 |
| 13 | 3-chloro phenyl | 224° C | Calculated | 60.9 | 3.10 | 7.9 | 10.0 |
| | | | Found | 61.0 | 3.1 | 8.0 | 10.1 |
| 14 | 2,4-dichloro phenyl | 225° C | Calculated | 55.5 | 2.57 | 7.19 | 18.25 |
| | | | Found | 55.4 | 2.50 | 7.12 | 18.3 |
| 15 | 4-(2,2,2-trifluoro ethoxy) phenyl | 230° C | Calculated | 57.4 | 3.11 | 6.69 | 13.6 |
| | | | Found | 57.4 | 3.2 | 6.66 | 13.5 |
| 16 | 2-(2,2,2-trifluoro ethoxy) phenyl | 168° C | Calculated | 57.4 | 3.11 | 6.69 | 13.6 |
| | | | Found | 57.4 | 3.18 | 6.35 | 14.2 |
| 17 | 2-difluoromethoxy phenyl | 204° C | Calculated | 59.0 | 3.10 | 7.25 | |
| | | | Found | 59.1 | 3.27 | 7.13 | |
| 18 | 4-mesyl phenyl | 258° C | Calculated | 57.2 | 3.51 | 7.03 | |
| | | | Found | 56.3 | 3.8 | 6.7 | |
| 19 | 3',5'-dimethyl 4-pyrazolyl (1') phenyl | 230° C | Calculated | 66.6 | 4.34 | 13.5 | |
| | | | Found | 66.4 | 4.4 | 13.2 | |

EXAMPLE 7

4.8 parts of 3-chloroformyl-7-methoxy coumarin and 2.9 parts of the amidoxime of cinnamic acid (melting point: 90° C) are stirred for one hour at ambient temperature in 30 parts of dimethylformamide, then the mixture is heated under reflux for 2 hours. By cooling, 2 parts of 7-methoxy-3-(3-styryl 1,2,4-oxadiazol-5-yl) coumarin with a melting point of 203° C. are separated by filtration.

| Analysis: | C % | H % | N % |
|---|---|---|---|
| Calculated for $C_{20}H_{14}N_2O_4$: | 69.36 | 4.04 | 8.09 |
| Found: | 69.6 | 4.28 | 7.91 |

EXAMPLE 8

The same operation is carried out as in Example 7, but the amidoxime of cinnamic acid is replaced by 2.7 parts of the amidoxime of 4-pyridinecarboxylic acid (melting point: 200° C). 0.9 part of 7-methoxy-3-[3-(4-pyridinyl) 1,2,4-oxadiazol-5-yl] coumarin is obtained with a melting point of 300° C.

| Analysis : | C % | H % | N % |
|---|---|---|---|
| Calculated for $C_{17}H_{11}N_3O_4$: | 63.55 | 3.42 | 13.08 |
| Found: | 63.4 | 3.41 | 13.1 |

The 4-trifluoromethoxy benzamidoxime (melting point: 94° C) used in Example 11 was prepared by the action of hydroxylamine on 4-trifluoromethoxy benzonitrile (Journal of General Chemistry USSR 27 page 518).

The 4-(2,2,2-trifluoro ethoxy) benzamidoxime (melting point: 148° C), the 2-(2,2,2-trifluoro ethoxy) benzamidoxime (melting point: 108° C) and the 2-difluoromethoxy benzamidoxime (melting point: 72° C) used for the preparation of the compounds in Examples 15, 16 and 17 were prepared by the action of hydroxylamine on the corresponding nitriles, namely 4-(2,2,2-trifluoro ethoxy) benzonitrile (melting point: 52° C), 2-(2,2,2-trifluoro ethoxy) benzonitrile (melting point: 70° C) and 2-difluoromethoxy benzonitrile (boiling point: 120° C/18 mm Hg) respectively. These nitriles may be prepared by the Sandmeyer reaction on 4-(2,2,2-trifluoro ethoxy) aniline (FIAT No. 1313, page 373), 2-(2,2,2-trifluoro ethoxy) aniline (FIAT No. 1313, page 373) and 2-difluoromethoxy aniline (J. General Chemistry USSR 1969, 39, Page 206).

The 3', 5'-dimethyl 4-pyrazolyl(1') benzamidoxime (melting point: 80° C) used in Example 19 was prepared by the action of hydroxylamine on 3', 5'-dimethyl 4-pyrazolyl (1')benzonitrile (melting point: 56° C) obtained by condensing N-(4-cyano phenyl) hydrazine with acetylacetone.

EXAMPLE 20

0.005 part of the compound obtained in Example 1 is dispersed in 100 parts of water with 0.01 part of the dispersing agent described in Example 1 or 4 of French Pat. No. 2,122,710. 1.25 parts of polyester fibres are dyed under pressure at 130° C. for one and a half hours in the dispersion obtained. After being rinsed and dried, the fibre thus treated exhibits a magnificent brightening effect with a rose-coloured reflection and with excellent general fastness.

The different compounds described in the other Examples given above, when applied to polyester fibres in similar conditions, produces brightening effects with similar properties.

I claim:
1. Coumarin of the formula:

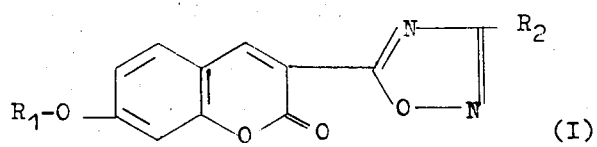

in which $R_1$ is alkyl containing 1 to 5 carbon atoms, said alkyl being unsubstituted or substituted by one chlorine, bromine, hydroxy or alkoxy containing 1–4 carbon atoms, $R_2$ is unsubstituted phenyl, phenyl substituted by one or two chlorine, bromine, alkyl containing 1–4 carbon atoms, alkylsulphonyl containing 1–4 carbon atoms, alkoxy containing 1–4 carbon atoms or fluoroalkoxy containing 1–4 carbon atoms or is 3- or 4-pyridyl, pyrazolyl, oxadiazolyl, or 3', 5'-dimethyl-4-pyrazolyl (1')-phenyl.

2. Coumarin according to claim 1 in which $R_2$ is unsubstituted phenyl or phenyl substituted by one or two chlorine, bromine, alkyl containing 1–4 carbon atoms, alkylsulphonyl containing 1–4 carbon atoms, alkoxy containing 1–4 carbon atoms or fluoroalkoxy containing 1–4 carbon atoms.

3. Coumarin according to claim 1 in which $R_2$ is the radical of formula:

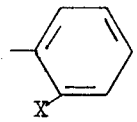

wherein X is hydrogen, chlorine, bromine, alkyl containing 1–4 carbon atoms, alkylsulphonyl containing 1–4 carbon atoms, alkoxy containing 1–4 carbon atoms or fluoroalkoxy containing 1–4 carbon atoms.

4. Coumarin according to claim 1 in which $R_3$ is 3- or 4-pyridyl.

5. 7-methoxy-3-(3-phenyl-1,2,4-oxadiazol-5-yl) coumarin.

6. 7-methoxy-3-(3-p-tolyl-1,2,4-oxadiazol-5-yl) coumarin.

7. 7-methoxy-3-[3-(2-chlorophenyl)-1,2,4-oxadiazol-5-yl] coumarin.

8. 7-methoxy-3-[3-(3-pyridinyl)-1,2,4-oxadiazol-5-yl] coumarin.

9. 7-methoxy-3- 3-[2-(2,2,2-trifluoroethoxy)-phenyl]-1,2,4-oxadiazol-5-yl coumarin.

* * * * *